(12) United States Patent
Dick et al.

(10) Patent No.: US 6,877,457 B1
(45) Date of Patent: Apr. 12, 2005

(54) IRREVERSIBLE HUMIDITY INDICATOR CARDS

(75) Inventors: Stefan O. Dick, Albuquerque, NM (US); Andrew J. Robertson, Albuquerque, NM (US); Michelle B. Martin, Palm Springs, CA (US)

(73) Assignee: Sud-Chemie Inc., Louisville, KY (US)

( * ) Notice: Subject to any disclaimer, the term of this patent is extended or adjusted under 35 U.S.C. 154(b) by 0 days.

(21) Appl. No.: 10/787,422

(22) Filed: Feb. 26, 2004

Related U.S. Application Data

(62) Division of application No. 09/660,560, filed on Sep. 12, 2000, now Pat. No. 6,698,378.

(51) Int. Cl.[7] .............................................. G01D 21/00
(52) U.S. Cl. ...................................... 116/206; 116/219
(58) Field of Search ................................ 116/206, 200, 116/207, 216, 217, 219, 201; 73/73, 29.04

(56) References Cited

U.S. PATENT DOCUMENTS

| | | |
|---|---|---|
| 2,214,354 A | 9/1940 | Snelling |
| 2,249,867 A | 7/1941 | Snelling |
| 2,460,065 A | 1/1949 | Davis |
| 2,460,066 A | 1/1949 | Davis |
| 2,460,067 A | 1/1949 | Davis |
| 2,460,068 A | 1/1949 | Davis |
| 2,460,069 A | 1/1949 | Davis |
| 2,460,070 A | 1/1949 | Davis |
| 2,460,071 A | 1/1949 | Davis |
| 2,460,072 A | 1/1949 | Davis |
| 2,460,073 A | 1/1949 | Davis |
| 2,460,074 A | 1/1949 | Davis |
| 2,526,938 A | 10/1950 | Davis |
| 2,580,737 A | 1/1952 | Davis |
| 2,627,505 A | 2/1953 | Goodwin |
| 2,716,338 A | 8/1955 | Blinn |
| 2,951,461 A | 9/1960 | Lockwood |
| 3,084,658 A | 4/1963 | Schell |
| 3,597,976 A | * 8/1971 | Fryar .......................... 116/219 |
| 3,680,364 A | 8/1972 | Carrier |
| 3,898,172 A | 8/1975 | Reif |
| 4,034,609 A | 7/1977 | Fuller |
| 4,050,307 A | 9/1977 | McMullen |
| 4,098,120 A | 7/1978 | Manske |
| 4,150,570 A | 4/1979 | Fuller |
| 4,205,043 A | 5/1980 | Esch |
| 4,793,180 A | 12/1988 | Stewart |
| 4,854,160 A | 8/1989 | Glatt |
| 5,061,258 A | * 10/1991 | Martz .......................... 604/307 |
| 5,224,373 A | 7/1993 | Williams |
| 5,875,892 A | 3/1999 | Martin |
| 5,964,181 A | 10/1999 | Pereyra |
| 5,997,927 A | 12/1999 | Gics |
| 6,698,378 B1 | 3/2004 | Dick |
| 2002/0000184 A1 | 1/2002 | Paton |
| 2003/0026818 A1 * | 2/2003 | Hoshino et al. ............ 424/401 |

OTHER PUBLICATIONS

W.B. Abel, Chemical Maximum Humidity Indicator Update Report, BDX-613-1989.

* cited by examiner

*Primary Examiner*—G. Bradley Bennett
*Assistant Examiner*—Travis Reis
(74) *Attorney, Agent, or Firm*—Scott R. Cox; Joan L. Simunic

(57) ABSTRACT

An irreversible humidity indicator card comprising an intermediate carrier member containing one or more holes, a clear, water vapor permeable first outer layer secured to the first side of the carrier member, a deliquescent material contained within the holes in the carrier member, a dark colored, absorbent sheet material secured to the back side of the carrier member to cover the holes in the carrier member and a second outer layer which covers the colored absorbent sheet material and a portion or all of the back side of the intermediate carrier member.

22 Claims, 2 Drawing Sheets

IRREVERSIBLE HUMIDITY INDICATOR CARDS

This application is a Divisional of application Ser. No. 09/660,560 filed on Sept. 12, 2000, now U.S. Pat. No. 6,698,378.

BACKGROUND OF THE INVENTION

1. Field of the Invention

This invention relates to humidity indicator cards and more particularly, to an irreversible humidity indicator card, which is covered on both sides, which utilizes a deliquescent material which does not contain a dye.

2. Description of Prior Art

When shipping or storing many types of materials, particularly electronic components, it is desirable to know whether those components have been exposed to a particular level of humidity which humidity could cause damage to those components. For example, electronic components can be damaged by exposure to low levels of humidity, even where the exposure is only for short periods of time. These same electronic components may also be contaminated and/or damaged by exposure to dust and other particulate matter.

To address the need for the detection of humidity levels within shipping or storage containers, humidity indicators have been developed. There are generally two types of humidity indicators. One of these humidity indicators reversibly changes color upon exposure to particular humidity levels. Such reversible humidity indicators typically utilize cobalt chloride as the humidity indicator material. It changes color when exposed to predetermined levels of humidity and returns to its original color when the humidity level drops below that predetermined level. These reversible humidity indicators are used to indicate the current condition of a desiccant and/or the current humidity level within the storage container.

The second type of humidity indicator is an irreversible humidity indicator. These indicators are designed to detect a predetermined level of humidity and provide a visual indication of whether components stored in the containers where these humidity indicators are used have been exposed to that predetermined level of humidity even for short periods of time and even if the level of humidity drops below that predetermined level when the components are checked at a later time. Large changes in humidity levels sometimes occur where storage containers are used in relatively warm climates where the moisture level in the air rises and falls dramatically depending upon the temperature of the surrounding air. Under these conditions, a reversible humidity indicator might fail to indicate the temporary presence of high humidity within a storage container even though such high humidity may be sufficient to cause damage to the components present in the storage container.

One of the first irreversible humidity indicator devices was disclosed in U.S. Pat. No. 2,214,354, which disclosed the use of a calcium chloride material which was mixed with a water soluble dye and deposited on a porous surface material, such as a sheet of absorbent paper. Upon exposure of the absorbent sheet to a predetermined humidity level, the calcium chloride material liquifies and releases the dye in liquid form. The dye is then carried by capillary action onto the porous surface of the absorbent paper, where it produces a permanent and irreversible dye mark. The aforementioned patent further describes various deliquescent agents which may be employed to show different humidity levels.

To maintain a consistently low humidity level, shipping containers and long term storage containers usually contain desiccant materials. These desiccant materials dehydrate the storage area and are intended to maintain the humidity level within that storage area at a predetermined level. These containers are periodically opened to recharge or replace the desiccant materials placed within the container and/or to check the level of humidity in the storage container. After replacing the desiccant material, the container is again sealed. In order to determine whether the humidity level in these storage containers has ever reached certain critical levels, irreversible humidity indicators are also often placed within the containers with the desiccant materials. These irreversible humidity indicators can be reviewed at the same time that the desiccant material is being checked to determine whether a harmful humidity level has ever been reached in the shipping container.

A series of relative humidity indicators, each utilizing a different deliquescent salt, are disclosed in a series of patents which were issued during the 1940's and 1950's including U.S. Pat. Nos. 2,460,065, 2,460,066, 2,460,067, 2,460,068, 2,460,069, 2,460,070, 2,460,071, 2,460,072, 2,460,073, 2,460,074, 2,526,938, 2,580,737, and 2,627,505. In addition, some humidity indicator cards are capable of showing different levels of humidity on the same card by use of a series of different deliquescent agents that change color at varying humidity levels, as disclosed in U.S. Pat. No. 2,249,867.

Humidity indicator sheets and cards which contain deliquescent salts and dyes have commonly been used to detect the relative humidity level present within storage containers. See for example, U.S. Pat. Nos. 2,249,867, 4,034,609, 4,150,570, and 4,854,160. Button-type humidity indicators or "plug" humidity indicators are also sometimes used with packaging material and are disclosed, for example, by U.S. Pat. Nos. 2,716,338, 3,084,658 and 4,050,307. Another device for monitoring humidity levels, particularly in poured cement, is disclosed in U.S. Pat. No. 3,680,364.

A multiple layer, reversible humidity sensing device containing a reflective layer, which is useful in viewing the changes in color of a humidity indicator card is disclosed by U.S. Pat. No. 4,034,609.

A reversible humidity indicator card contained within transparent, flexible sheet materials with an impermeable front layer is disclosed in U.S. Pat. No. 5,224,373. This humidity indicator card is specifically designed for utilization with electronic components. It is formed as a "window" in a barrier bag.

A delayed action, irreversible humidity indicator card is disclosed in U.S. Pat. No. 4,793,180.

All irreversible humidity indicator cards known hitherto are based on combinations of deliquescent salts and water-soluble dyes. In order to prepare humidity indicator cards that react at various humidity levels, different combinations of deliquescent salts and dyes must be chosen. Only cards that show the same change in color at each chosen humidity level are acceptable to users of these cards. Otherwise, if there are varying color changes, it may be difficult to determine whether a particular humidity level has been reached. W. B. Abel: *Chemical Maximum Humidity Indicator Update Report*, BDX-613-1989 and U.S. Pat. No. 3,898,172 teach that only certain combinations of salts and dyes are useful for this purpose as the dye is quite soluble in the saturated salt solution that is formed upon deliquescence. In addition, the solubility and color of the dye must be independent of pH changes that may be attributed to the deliquescence of the salt. To ensure a proper shelf-life of the indicator card, the dye also must not react with the salt in any way (e.g. redox reaction, acid-base reaction). It is quite difficult to use either the same dye or different dyes with the same color and different salts over the entire humidity spectrum.

Mixing the individual salts with the dye is an additional required step for the production of the irreversible humidity indicators previously known. If the chosen salt and dye have different particle sizes, inhomogeneous distribution of the dye in the salt may occur and lead to inhomogeneous color and appearance on the indicating spot of the humidity indicator. This problem can be overcome by milling salt and dye together, but this is not possible for all salt—dye combinations, especially if the salt already holds water of crystallization.

Further, many of the deliquescent salts when they absorb moisture and melt can cause corrosion to the products stored in the shipping containers in which the humidity indicator cards are utilized.

In addition, the blotter paper used to form conventional humidity indicator cards sometimes sheds paper fibers and lint. Such fibers and lint may damage products that are sensitive to dust, such as electronic components.

Accordingly, it is an object of this invention to produce an irreversible humidity indicator card which solves the problems present with conventional irreversible humidity indicator cards.

It is a still further object of the invention to disclose an irreversible humidity indicator card which is formed of a composite structure which includes a darkened blotter paper which is useful in showing a predetermined level of humidity.

It is a further object of the invention to disclose an irreversible humidity indicator card which does not use a dye with its deliquescent material.

It is a further object of the invention to disclose an irreversible humidity indicator card which does not produce paper fibers or lint when in use.

SUMMARY OF THE INVENTION

This invention is directed to an irreversible humidity indicator card comprising
  an intermediate carrier member, containing front and back sides and one or more holes passing through the member,
  a water vapor permeable, first outer layer completely covering the front side of the intermediate carrier member,
  a deliquescent material placed within the holes in the intermediate carrier member,
  a colored absorbent sheet material, placed against the back side of the intermediate carrier member, which sheet material covers the holes in the intermediate carrier member, and
  a second outer layer secured to the back side of the intermediate carrier member, which covers the colored absorbent material and covers the back side of the intermediate carrier member.

Preferably, the colored absorbent material is a darkened blotting paper which absorbs the deliquescent material when the deliquescent material absorbs moisture and liquifies.

In another preferred embodiment, the water vapor permeable first outer material and/or the second outer layer further comprise materials with anti-static and/or electrostatic charge dissipative properties.

The invention is also directed to a process for the production of the above-referenced irreversible humidity indicator card comprising
  preparing an intermediate carrier member containing a front and back side and one or more holes passing through the member,
  securing a clear, water vapor permeable, outer layer to the front side of the intermediate carrier member,
  placing a deliquescent material within the holes of the intermediate carrier member,
  covering the holes of the carrier member on the back side of the intermediate carrier member with a colored, absorbent sheet material, preferably a blotter paper, and
  covering the colored, absorbent sheet material and the back side of the intermediate carrier member with a second outer layer.

Alternatively, the colored, absorbent sheet material may first be secured to the second outer layer prior to securing that second outer layer to the back side of the intermediate carrier member.

DESCRIPTION OF A PREFERRED EMBODIMENT

Figure 1:
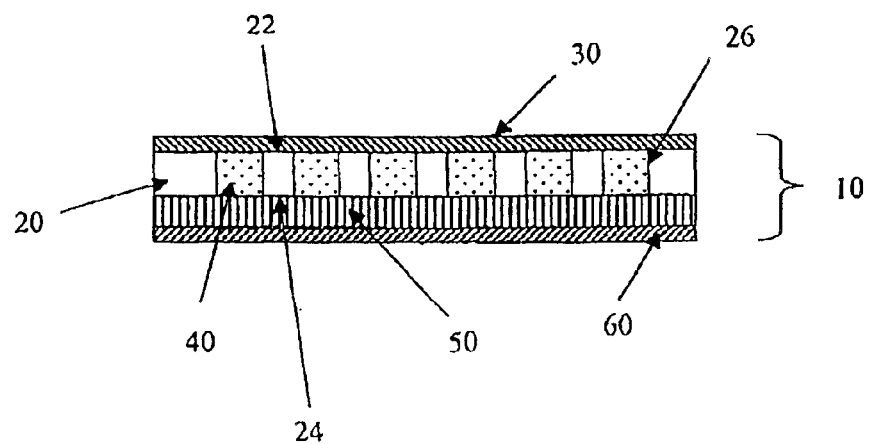
FIG. 1 is a side view of the irreversible humidity indicator card of the invention.
Figure 2:
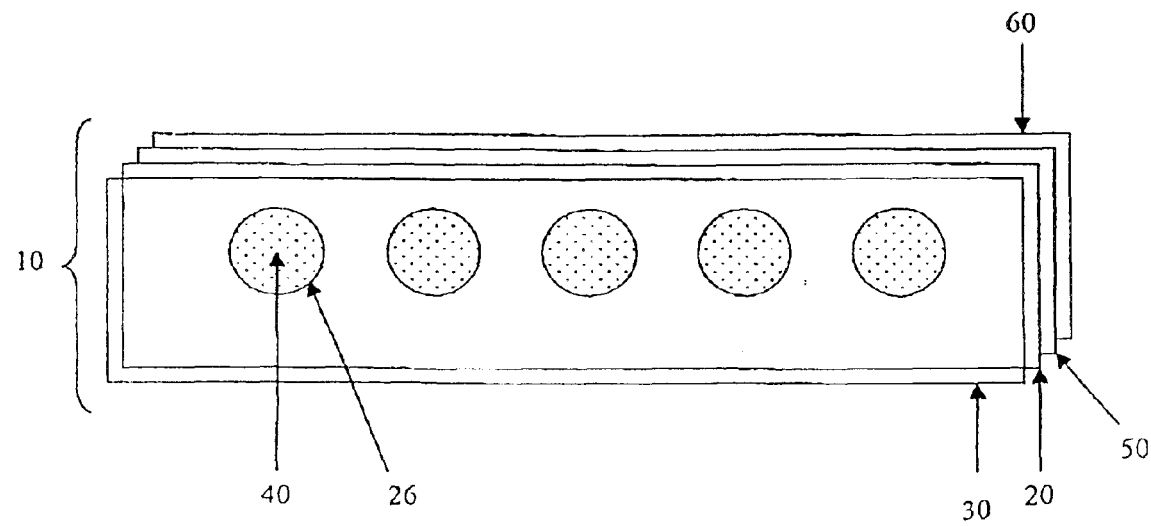
FIG. 2 is a perspective, exploded front view of the irreversible humidity indicator card.
Figure 3:
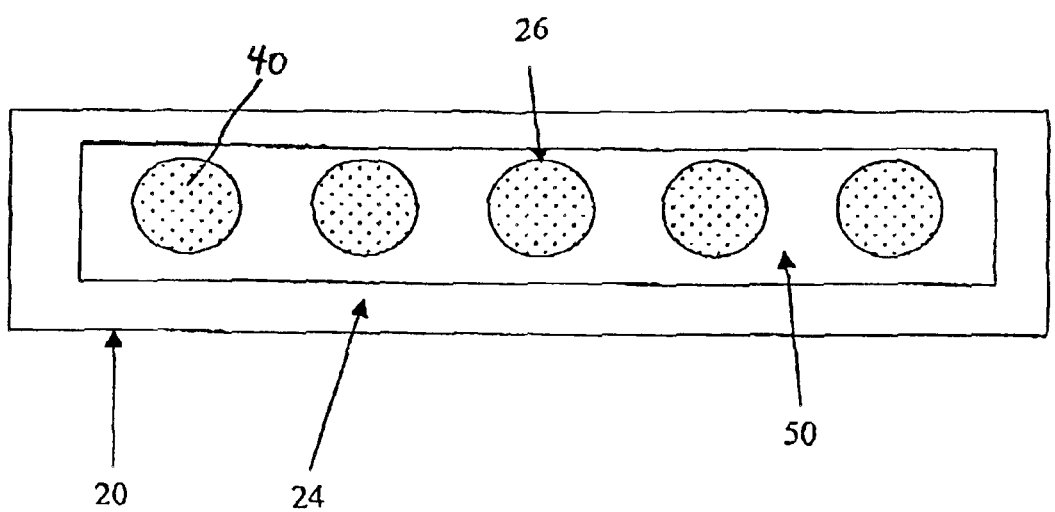
FIG. 3 is a back view of the irreversible humidity indicator card without the second outer layer (60).

Referring to FIGS. 1, 2 and 3, the invention is an irreversible humidity indicator card (10) comprised of an intermediate carrier member (20), a first outer layer (30), deliquescent material (40), a colored absorbent sheet material (50) and a second outer layer (60). The intermediate carrier member (20) contains a front side (22) and back side (24) and a series of holes (26) which pass through the intermediate carrier member (20) from its front (22) to its back side (24). The first outer layer (30) is secured to the front side (22) of the intermediate carrier member (20). The colored absorbent sheet material (50) is placed against the back side (24) of the intermediate carrier member (20). The deliquescent material (40) is placed within the holes (26) of the intermediate carrier member (20) and is held in place between the first outer layer (30) and the colored absorbent sheet material (50). The second outer layer (60) entirely covers the colored absorbent sheet material (50) and preferably covers the entire back side (24) of the intermediate carrier member (20).

The intermediate carrier member is preferably formed from a single sheet of a moisture absorbent material, such as a conventional blotter paper. One or more holes (26) are cut through the intermediate carrier member (20) with the number and placement of the holes (26) dependent on the need of the manufacturer of the humidity indicator cards (10). Written information informing the user of the humidity indicator card (10) about the humidity levels determined by the humidity indicator card (10) is generally printed on the front side (22) of the intermediate carrier member (20).

The front side (22) of the intermediate carrier member (20) is entirely covered by the first outer layer (30). The first outer layer is preferably a thin, clear, water vapor permeable plastic film material. This first outer layer (30) is preferably formed from thin, clear plastic film having a moisture vapor transmission rate of at least about 1 g/(m²•day), preferably more than about 10 g/(m²•day) and most preferably more than 100 g/(m²•day). Well known plastic films with these characteristics which may be used include cellulose derivatives like cellophane, cellulose acetate, cellulose nitrate and cellulose acetobutyrate, polyurethane elastomers, polyamides like polyamide 6 and polyamide 66, polyvinylflouride, plastified polyvinylchloride, polystyrenes, polysiloxanes, ethylene-vinylalcohol-copolymers and polyesters. Alternatively, clear microporous films comprised of plastic materials may be used. The type of material used for these films and the thickness of the films determine the moisture transmission rate through the first outer layer. By carefully selecting these parameters, permeation of water vapor through the first outer layer is quick enough to cause a response from the deliquescent material (40) and therefore indicate the humidity level of the surrounding air within the time predetermined by the manufacturer of the humidity indicator card (10). One preferred first outer layer (30) is a thin cellophane material. Alternatively, a thin polyester material or a thin flexible PVC material may be used.

One side of the clear, thin, water vapor permeable first outer layer (30) is coated with an adhesive material, such as a rubber adhesive, an acrylic adhesive or a silicone adhesive. This adhesive is used to secure the first outer layer (30) to the front side (22) of the intermediate carrier member (20). Preferably, the first outer layer (30) should completely cover the front side (22) of the intermediate carrier member (20). This prevents any dust, lint or deliquescent material from escaping from the front side (22) of the intermediate carrier member (20). In one embodiment the edges of the first outer layer (30) extend beyond the edges of the intermediate carrier member (20) so that the edges of the first outer layer (30) can be secured to edges of the second outer layer (60) and thus, completely encapsulate the intermediate carrier member (20).

Deliquescent materials (40) are placed within each of the openings (26) that are cut through the intermediate carrier member (20). The composition of the deliquescent materials (40) that are placed in each of the holes (26) may be the same or it may be different. The various deliquescent materials (40) may liquify at the same or different humidity levels. The choice as to the particular deliquescent material (40) depends on the manufacturer of the humidity indicator card (10). A list of deliquescent salts that may be useful can be found in W. B. Abel: "*Chemical Maximum Humidity Indicator Update Report*", BDX613-1989 and includes $ZnCl_2$, $ZnBr_2$, $ZnI_2$, $LiCl$, $LiBr$, $LiI$, $KC_2H_3O_2$, $CaCl_2$, $Zn(NO_3)_2$, $KNO_2$, $KNCS$, $NaHSO_4$, $NaBr$, $NaNO_2$, $Mg(C_2H_3O_2)_2$, $NaClO_2$, $NaC_2H_3O_2$, $Na_2S_2O_3$, $NHCl_4$, $(NH)_4SO_2$, $KBr$, $KHSO_4$, $ZnSO_4$, $NaBrO_3$, $Na_2SO_4$ and $Na_2SO_3$. Either a single deliquescent salt or a combination of two or more deliquescent salts may be used as the deliquescent material which indicates a defined humidity level. Alternatively, a single deliquescent salt or a mixture of two or more deliquescent salts may be combined with one or more non-deliquescent salts and/or non-ionic compounds to be used as the deliquescent material to indicate a defined humidity level.

The deliquescent material (40) is preferably white when dry and preferably does not contain a dye. When placed in the holes (26) of the intermediate carrier member (20), the deliquescent material (40) should completely cover the colored absorbent sheet material (50) showing through from the back side (24) of the intermediate carrier member (20) until the deliquescent material (40) liquifies and is absorbed by the colored absorbent sheet material (50). Thus, the holes (26) of the intermediate carrier member (20) appear white until the deliquescent material (40) present in those holes (26) liquifies. After the deliquescent material (40) liquifies and is absorbed by the colored absorbent sheet material (50), the dark color of the absorbent sheet material (50) shows through the holes (26) in the intermediate carrier member (20).

The back side (24) of the intermediate carrier member (20) is at least partially covered by the colored absorbent sheet material (50) as shown in FIG. 3. This colored absorbent sheet material (50) should, at minimum, cover each of the holes (26) which are cut into the intermediate carrier member (20). The colored absorbent sheet material (50) may cover only the holes (26) or it may cover up to the entire back side (24) of the intermediate carrier member (20). Preferably, the colored absorbent sheet material (50) is formed in a horizontal strip which covers only a portion of the back side (24) of the intermediate carrier member (20) as shown in FIG. 3. This colored absorbent sheet material (50) is preferably formed from a blotter paper similar in construction to that of the intermediate carrier member (20). Preferably this colored absorbent sheet material (50) is colored a dark color, such as red, green or black so that its color shows through when its deliquescent material (40) melts and is absorbed by the colored absorbent sheet (50) and the intermediate carrier member (20). The colored absorbent sheet material (50) may be first secured to the second outer layer (60) prior to securing the second outer layer (60) to the intermediate carrier member (20). Alternatively, the colored absorbent sheet (50) can be first placed next to the back side (24) of the intermediate carrier member (20) with the second outer layer (60) and then secured to the back side (24) of the intermediate carrier member (20). In a further alternative, the colored absorbent sheet (50) may be secured to the back side (24) of the intermediate carrier member (20) by a conventional securing system, such as by use of an adhesive.

The second outer layer (60) at least covers the colored absorbent sheet material (50) and is secured to the back side (24) of the intermediate carrier member (20). While the second outer layer (60) need not entirely cover the back side (24) of the intermediate carrier member (20), in one preferred embodiment the second outer layer (60) does entirely cover the back side (24) of the intermediate carrier member (20). The second outer layer (60) is secured in position against the intermediate carrier member (20) with an adhesive which also binds that second outer layer (60) to the colored absorbent sheet material (50).

This second outer layer (60) may be produced from the same material that is used for the first outer layer (20) or from different materials. Preferably it is an opaque plastic material which diffuses or partially diffuses the color of the colored absorbent sheet (50). In addition, this second outer layer (60) may have the same water vapor transmission rate as does the water vapor permeable first outer layer (30) or it may have a lower water vapor permeability. Preferably, it has a moisture transmission rate of at least about 1 g/(m²•day), more preferably, more than 10 g/(m²•day) and is formed from an opaque, white or colored, plastic material. The second outer layer (60) may be prepared from a well-known plastic material such as cellulose derivatives like cellophane, cellulose acetate, cellulose nitrate and cellulose acetobutyrate, polyurethane elastomers, polyamides like polyamide 6 and polyamide 66, polyvinylflouride, plastified polyvinylchloride, polystyrenes, polysiloxanes, ethylene-vinylalcoholcopolymers and polyesters. Preferably an opaque or colored polyester material or a thin flexible PVC material is used.

In an alternative embodiment, the composition of the irreversible humidity indicator (10) also preferably includes a material which introduces electrostatic charge dissipating and/or anti-static properties to the irreversible humidity indicator (10). The material which introduces electrostatic dissipating and/or anti-static properties may be incorporated into the clear water vapor permeable first outer layer (30) and/or into the second outer layer (60). The material which introduces electrostatic charge dissipating and/or anti-static properties is preferably selected from the group consisting of carbon products, anionic surfactants, cationic surfactants, amines, amides, ethoxylated fatty amines, ethoxylated fatty amides and hydrophilic graft copolymers. In one preferred embodiment a carbon black, such as Printex XE 2, produced by Degussa, is incorporated into the second outer layer (60). Alternatively, the clear water vapor permeable first outer layer (30) and/or the second outer layer (60) may consist of plastic material that is electrostatic charge dissipative by nature, such as cellulose derivatives.

In the process of formation of the irreversible humidity indicator card (10), the intermediate carrier member (20), which is preferably a conventional blotting paper, is first formed into a card shape with holes (26) cut in it which are designed to hold the deliquescent material (40). The clear water vapor permeable first outer layer (30) is then secured to the front side (22) of the intermediate carrier member (20), preferably by use of a conventional adhesive material. The deliquescent material (40) is then placed within the holes (26) in the intermediate carrier member (20), completely filling those holes (26). The deliquescent material (40) is held in place by covering the holes (26) on the back side (24) of the intermediate carrier member (20) with the colored absorbent sheet material (50). The colored absorbent sheet material (50) is held in place against the intermediate carrier member (20) either by use of an adhesive secured to the colored absorbent sheet material (50) or, more preferably, it is held in place by an adhesive being placed on one side of the second outer layer (60) and securing that second outer layer (60) to the back side (24) of the intermediate carrier member (20). Regardless, after the colored, absorbent sheet material (50) is in place against the back side (24) of the intermediate carrier member (20), the deliquescent material (40) substantially covers the portion of the colored absorbent sheet material (50) that shows through the holes (26), thereby substantially preventing the dark color of the colored absorbent sheet material (50) from showing through to the front side (22) of the intermediate carrier member (20). Preferably, the second outer layer (60) completely covers the back side (24) of the intermediate carrier member (20). It may even extend over the edges of the back side (24) of the intermediate carrier member to be secured to the clear, water vapor permeable first outer layer (30).

In use, this card (20) can be placed in a shipping container or storage container for equipment, preferably electronic equipment or electronic components, such as integrated circuits. Humidity present in the air within the container passes through at least the clear, water vapor permeable, first outer layer (30) to be absorbed by the deliquescent material (40). Moisture may also pass through the second outer layer (60) and the adsorbent sheet material (50) to contact the deliquescent material (40) depending on the choice of material for those layers. Once sufficient moisture is absorbed by the deliquescent material (40), the deliquescent material (40) liquifies and is absorbed by the colored absorbent sheet material (50) and possibly by the intermediate carrier member (20). Because the absorbent sheet material (50) is colored a dark color and the deliquescent material (40) is white in its powder form, the dark color of the absorbent sheet material shows through the holes (26) in the intermediate carrier member (20) only after the deliquescent material (50) liquifies. Once liquification occurs, the humidity indicator card (10) shows that the predetermined moisture level stated on the card (10) has been reached. By encapsulation of the deliquescent material (40) between the first outer layer (30) and the colored absorbent sheet material (50), which is secured to the second outer layer (60), no leakage of the melted deliquescent material (40) can occur into the shipping or storage containers.

The principles, preferred embodiments and modes of operation in the present invention have been described in the aforementioned specification. The invention, which is intended to be protected herein, is not to be construed as limited to the particular structures or embodiments disclosed, as these are to be regarded as illustrative rather than restrictive. Variations and changes may be made by those skilled in the art without departing from the invention.

We claim:

1. An irreversible humidity indicator card, comprising
   an intermediate carrier member, containing one or more holes passing through the intermediate carrier member,
   a water vapor permeable, clear, first outer layer secured to a front side of the intermediate carrier member,
   a deliquescent material contained within the holes in the intermediate carrier member,
   a dark colored, absorbent sheet material placed against a back side of the intermediate carrier member, which material covers the holes in the intermediate carrier member, and
   a second outer layer, secured to the back side of the intermediate carrier member, which covers the colored, absorbent sheet material.

2. The irreversible humidity indicator card of claim 1, wherein the water vapor permeable, first outer layer is coated on one side with an adhesive material.

3. The irreversible humidity indicator card of claim 1 wherein the second outer layer is comprised of a water vapor permeable material.

4. The irreversible humidity indicator card of claim 1 wherein the second outer layer is coated with an adhesive material.

5. The irreversible humidity indicator of claim 1 wherein the second outer layer completely covers the back side of the intermediate carrier member.

6. The irreversible humidity indicator card of claim 1 wherein the deliquescent material is selected from the group consisting of a single deliquescent salt, a mixture of two or more deliquescent salts, a mixture of a single deliquescent salt with one or more non-deliquescent salts, a mixture of two or more deliquescent salts and one or more non-deliquescent salts, a mixture of a single deliquescent salt with one or more non-ionic compounds and a mixture of two or more deliquescent salts with one or more non-ionic compounds.

7. The irreversible humidity indicator card of claim 1 further comprising a plurality of deliquescent materials, each of which liquifies at a different, predetermined humidity level.

8. The irreversible humidity indicator card of claim 1 wherein the clear, water vapor permeable first outer layer has a vapor transmission rate of at least about 1 g/($m^2$·day).

9. The irreversible humidity indicator card of claim 1 wherein the colored, absorbent sheet material is produced from a colored blotting sheet.

10. The irreversible humidity indicator card of claim 1 wherein the second outer layer covers the back side of the intermediate carrier member.

11. The irreversible humidity indicator card of claim 1 wherein the second outer layer is secured at one or more of its edges to the clear, water vapor permeable, first outer layer.

12. The irreversible humidity indicator card of claim 1 wherein the dark colored, absorbent sheet material is colored with a dark color, such as red, green or black.

13. The irreversible humidity indicator card of claim 1 wherein the color of the absorbent sheet material shows through the openings in the intermediate carrier member and the clear, first outer layer when the deliquescent material melts and is absorbed by the absorbent sheet material.

14. An irreversible humidity indicator card, comprising
an intermediate carrier member, containing one or more holes passing through the intermediate carrier member,
a water vapor permeable, clear, first outer layer secured to a front side of the intermediate carrier member,
a white deliquescent material contained within the holes in the intermediate carrier member,
a dark colored, absorbent sheet material placed against a back side of the intermediate carrier member, which material covers the holes in the intermediate carrier member, and
a second outer layer, secured to the back side of the intermediate carrier member, which covers the colored, absorbent sheet material.

15. The irreversible humidity indicator card of claim 12 wherein the dark colored, absorbent sheet material is colored with a dark color, such as red, green or black.

16. An irreversible humidity indicator card, comprising
an intermediate carrier member, containing one or more holes passing through the intermediate carrier member,
a water vapor permeable, clear, first outer layer secured to a front side of the intermediate carrier member,
a deliquescent material contained within the holes in the intermediate carrier member, wherein the deliquescent material does not include a dye material,
a dark colored, absorbent sheet material placed against a back side of the intermediate carrier member, which material covers the holes in the intermediate carrier member, and
a second outer layer, secured to the back side of the intermediate carrier member, which covers the colored, absorbent sheet material.

17. The irreversible humidity indicator card of claim 13 wherein the dark colored, absorbent sheet material is colored with a dark color, such as red, green or black.

18. A process of manufacture of a humidity indicator card comprising
preparing an intermediate carrier member containing one or more holes, a front side and a back side,
securing a clear, water vapor permeable, first outer layer to the front side of the intermediate carrier member,
placing a deliquescent material within the holes of the intermediate carrier member,
covering the holes of the carrier member on the back side of the intermediate carrier member with a dark colored absorbent material, and
covering the colored absorbent material and the back side of the intermediate carrier member with a second outer layer.

19. The process of claim 18 wherein the deliquescent material does not include a dye material.

20. A process of manufacture of a humidity indicator card comprising
preparing an intermediate carrier member containing one or more holes and a front side and a back side,
securing a clear, water vapor permeable, first outer layer to the front side of the intermediate carrier member,
placing a deliquescent material within the holes of the intermediate carrier member,
securing a dark colored, absorbent sheet material to a second outer layer, and
securing the second outer layer with attached colored absorbent sheet to the back side of the intermediate carrier member, wherein the colored absorbent sheet material covers the holes in the intermediate carrier member.

21. The process of claim 20 wherein the deliquescent material does not include a dye material.

22. An irreversible humidity indicator card, comprising
an intermediate carrier member, containing one or more holes passing through the intermediate carrier member,
a water vapor permeable, clear, first outer layer secured to a front side of the intermediate carrier member,
a deliquescent material contained within the holes in the intermediate carrier member which liquifies at a pre-determined humidity level,
a dark colored, absorbent sheet material placed against a back side of the intermediate carrier member, which absorbent material covers the holes in the intermediate carrier member and is capable of absorbing the liquified deliquescent material when it liquifies, and
a second outer layer, secured to the back side of the intermediate carrier member, which covers the colored, absorbent sheet material.

* * * * *